United States Patent [19]

Sawamura et al.

[11] 4,154,652

[45] May 15, 1979

[54] METHOD FOR AUTOMATICALLY AND SUCCESSIVELY CULTIVATING TISSUES OR CELLS OF A BODY

[75] Inventors: Ichiro Sawamura; Shinroku Sogi, both of Hachiouji; Shin-ichi Kamachi, Hino; Makoto Yoshinaga, Hachiouji; Atsuo Goto, Tachikawa; Masao Izawa, Hachiouji; Yoshio Nakajima, Hachiouji; Nagahiro Gocho, Hachiouji; Toshio Shinohara, Chofu; Shinichiro Hattori, Tokyo, all of Japan

[73] Assignee: Olympus Optical Co., Ltd., Tokyo, Japan

[21] Appl. No.: 694,643

[22] Filed: Jun. 10, 1976

[30] Foreign Application Priority Data

Jun. 20, 1975 [JP] Japan .............................. 50-76256

[51] Int. Cl.² .......................... C12K 9/00; C12K 1/10
[52] U.S. Cl. ................................. 195/1.8; 195/127; 195/1.7
[58] Field of Search .................... 195/1.8, 127, 1.7

[56] References Cited

U.S. PATENT DOCUMENTS

| | | | |
|---|---|---|---|
| 2,975,553 | 3/1961 | Paul | 195/1.7 |
| 3,887,436 | 6/1975 | Haddad et al. | 195/1.7 |
| 3,959,074 | 5/1976 | Miller et al. | 195/1.8 |
| 3,962,041 | 6/1976 | Muller et al. | 195/127 |

*Primary Examiner*—Sam Rosen
*Attorney, Agent, or Firm*—Cushman, Darby & Cushman

[57] ABSTRACT

Tissues or cells of a living body, especially a human body, are automatically and successively cultivated in a nutrient solution filled culture container disposed in a gas-sealed culture box by detecting, within the culture box, a multiplication condition of the tissues or cells and culture conditions which are represented by temperature, humidity and gaseous atmosphere in the culture box and pH value of the nutrient solution, controlling the culture conditions and apparatus for subculture of the tissues or cells within the culture box in accordance with the information detected.

1 Claim, 2 Drawing Figures

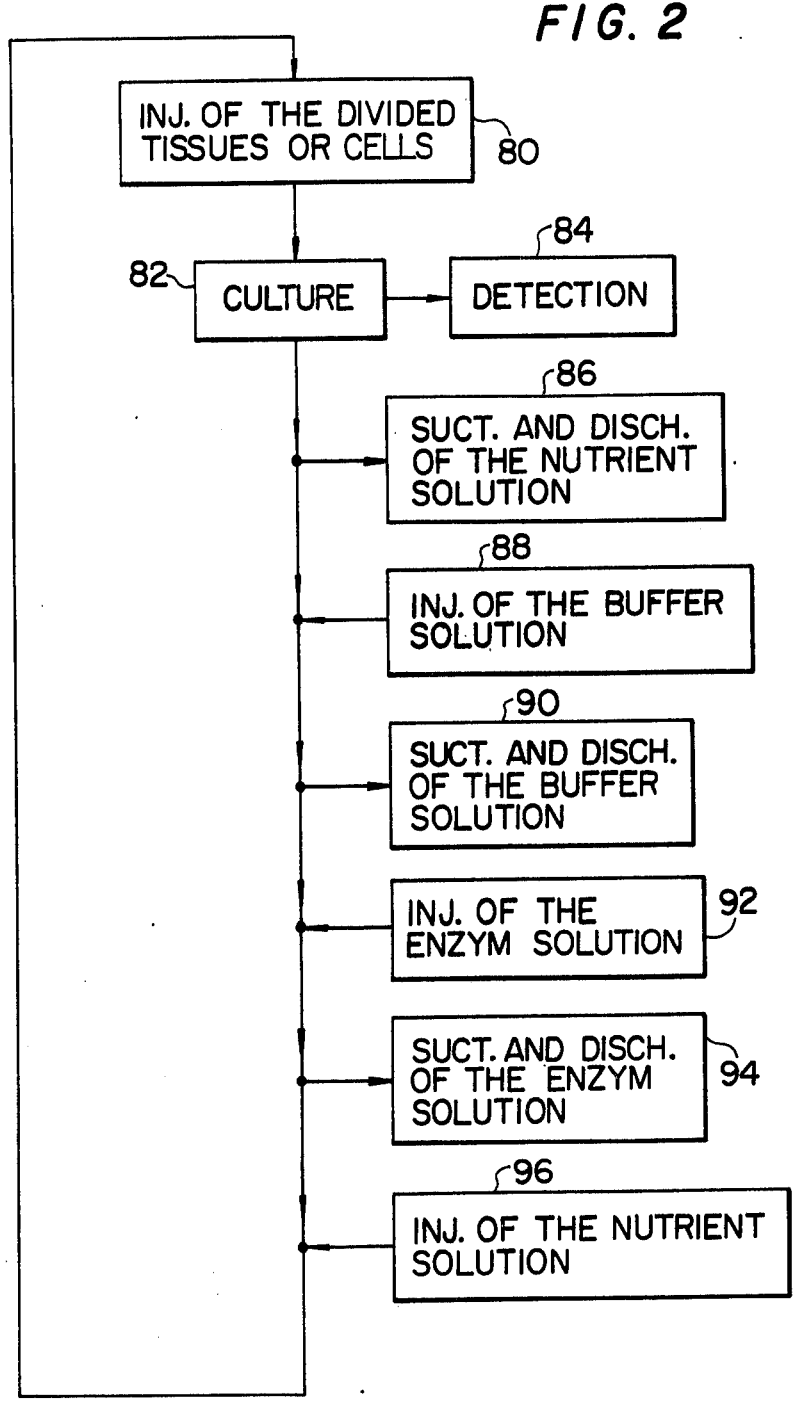

METHOD FOR AUTOMATICALLY AND SUCCESSIVELY CULTIVATING TISSUES OR CELLS OF A BODY

BACKGROUND OF THE INVENTION

1. Field of the Invention

The present invention relates to a method for automatically and successively cultivating tissues or cells of a living body, and more particularly to such method for cultivating the tissues or cells under controlled conditions in a gas-sealed culture box excluding bacteria contamination.

2. Description of the Prior Art

In the present instance, the techniques for the culture of such tissues, especially cells of a living body have been of fundamental importance in many fields such as medicine, biology and related fields.

On the other hand, recent developments or advances in the study of viruses and rickettsia have enabled scientists to produce a variety of new vaccines. These vaccines must be steadily produced for the needed amount of products which are stable in quality Heretofore, though the vaccines are usually produced by using hen's eggs as a culture base, it is desirable for the culture base to be tissues or cells of a human body from the immunological point of view. It is known, that a person who is repeatedly inoculated with the egg-based vaccines produced by the conventional manner sometimes may develop an egg allergy. This has been one of the problems to which the present invention is directed and necessitates a large quantity of tissues or cells of the human body, which were cultured by a standardized manner.

Due to the difficulty of subculturing the tissues or cells of the human body, it was previously believed that a stable cultivated "mass" of such tissues or cells can not be obtained except for the specific cells or tissues; later the technique for cultivating the tissues or cells of the living body in an incubator or a culture box, the inside of which is maintained in a specific gaseous atmosphere, was developed. Due to this culture technique, it has become possible to cultivate even the distinctive cells of the human body such as liver cells, nerve cells and hypophysis cells.

However, the conventional tissue or cell culture technique is difficult to standardize for the reasons described hereinafter. In the cell or tissue culture technique in a gaseous atmosphere, which is believed the most effective method at the present instance in this field, it is inevitably necessary to frequently remove the culture container containing the tissues or cells from the gas-sealed culture box or the incubator during the cultivation in order to microscopically observe the multiplication conditions of the tissues or cells. According to the results of such observation, a technician who is skilled in the cell or tissue culture technique then performs the necessary manipulation for the subculture of the cells or tissues. Therefore, the cells or tissues in the culture container are exposed to the air for considerably long periods of time during such observation and manipulation, and thus the culture environment for the cells or tissues will be greatly changed. In addition to these changes of the culture conditions, the cells or tissues will be contaminated by the air itself and any bacteria or germs that may be contained in the air. Furthermore, the number of technicians who are skilled in the cell or tissue culture technique is quite insufficient, since at least two years is needed for training.

Since the standardization of the cell or tissue culture is very difficult for the reasons described above, completely opposite conclusions are sometimes obtained by different scientists who have respectively studied the same item.

Therefore, instead of a technician a scientist must spare his time and attention for the cell or tissue culture which is not his essential work, instead of devoting his effort to original medical or biological studies. This is a common concern among scientists of various fields, and thus the unification, standardization and automation of the cell or tissue culture are needed.

SUMMARY OF THE INVENTION

Therefore, it is a primary object of the present invention to provide a method for cultivating tissues or cells of the living body, which enables the cell or tissue culture technique to be unified, standardized and automated and which technique avoids possible contaminations by the air or bacterias in the air during the cultivation.

Another object of the present invention is to provide a method for cultivating tissues or cells of the living body, with which the tissues or cells are automatically and successively cultivated in large quantities.

These objects and other objects of the present invention are attained by providing, when cultivating tissues or cells of a living body which are contained together with a nutrient solution in a culture container disposed in a gas-sealed culture box, detecting within the culture box a multiplication condition of the tissues or cells and culture conditions represented by temperature, humidity and gaseous atmosphere in the culture box and pH value of the nutrient solution. Further a controlling step with which the culture conditions and apparatus for subculture of the tissues or cells are controlled in accordance with the information obtained by the detecting step.

According to the present invention, the tissues or cells of the living body can be favourably cultivated without contamination such as bacterial contamination, since the tissues or cells are not exposed to the air during the cultivation. Furthermore, according to the present invention, unification or standardization of the culture conditions can be realized by the present invention, since the gaseous atmosphere, temperature, humidity, pH value of the nutrient solution, and necessary apparatus for subculture are automatically controlled by means of the information obtained by continuously detecting the state of the culture and culture conditions, and thereby obviating the need for special technicians to process the subculture

BRIEF DESCRIPTION OF THE DRAWINGS

Other objects and features of the invention will become apparent to those skilled in the art from the following description of a preferred embodiment of the invention, as illustrated in the accompanying sheet of drawings and wherein, FIG. 1 schematically shows the culture apparatus for embodying the method according to the present invention and FIG. 2 diagrammatically shows the process of the tissue or cell culture according to the present invention.

DESCRIPTION OF THE PREFERRED EMBODIMENT

Figure 1:
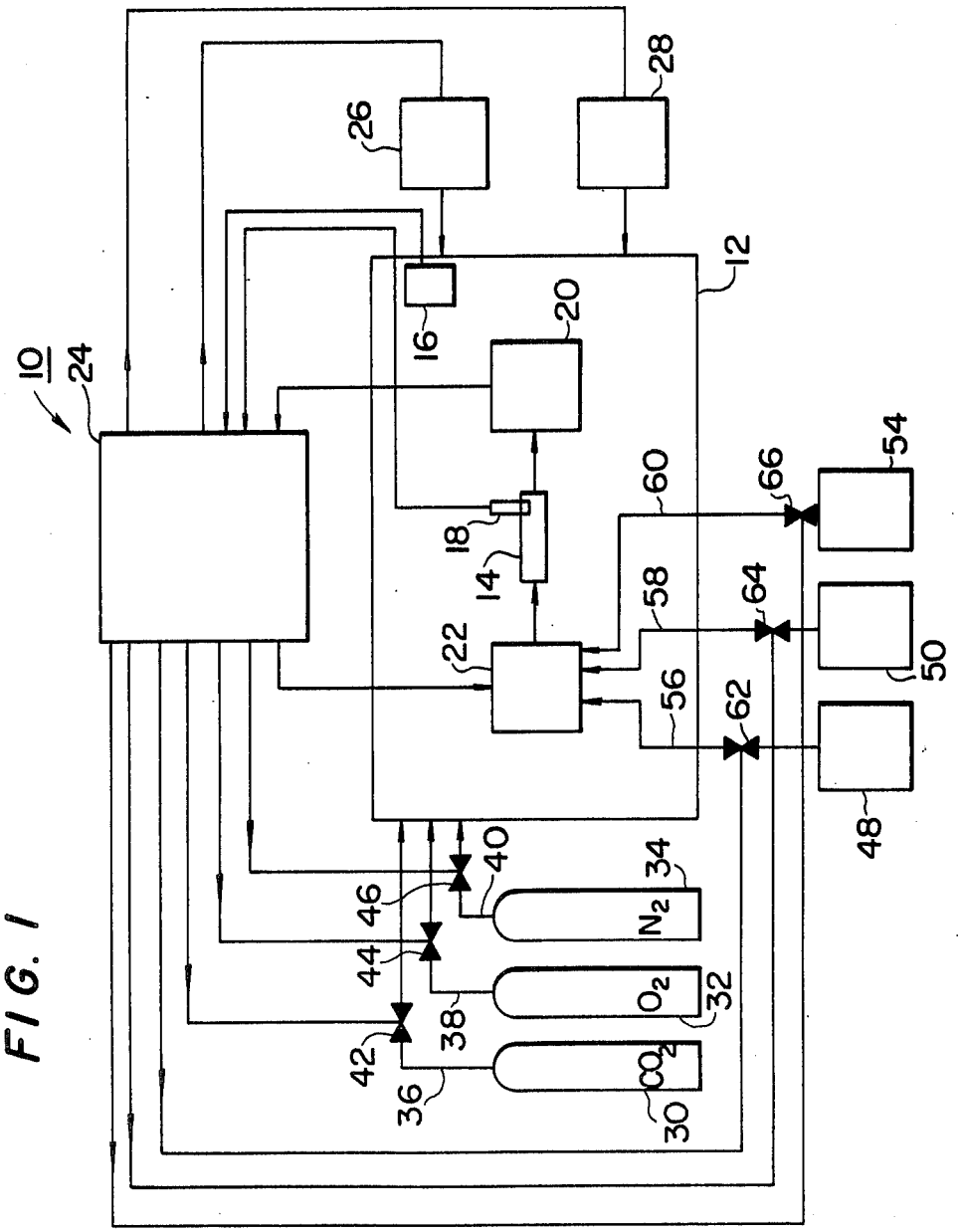

Referring now to FIG. 1, there is shown schematically and diagrammatically a culture apparatus 10 for carrying out the method for cultivating cells or tissues of a living body according to the present invention. The culture apparatus 10 comprises a gas-sealed culture box 12 in which a plurality of culture containers 14 such as Petri dishes are disposed. Each one of the containers 14 contains cells or tissues (not shown) of the living body therein together with a nutrient solution. Disposed within the culture box 12 are a first detector means 16 for detecting the gaseous atmosphere, temperature and humidity within the box 12, a second detector means 18 for detecting the pH value of the nutrient solution in each container 14 and a third detector means 20 mainly composed of an optical microscope for detecting the multiplication conditions of the cells or tissues in each container 14. The third detector means 20 is fixedly mounted at a preselected position within the culture box 12, and each of the containers 14 is successively moved by a moving mechanism (not shown) to the position where the detector means 20 can detect the multiplication conditions of the cells or tissues in each container 14. In this case, the objective lens of the microscope of the detector means 20 may be lodged for the detection into the nutrient solution or the tissues or cells in the container 14 as described in Japanese published patent specification No. 12945/1976. A distributing means 22 is also disposed within the box 12, which serves to distribute a nutrient solution, a buffer solution and an enzyme solution into each container 14 and to discharge these solutions from the container 14 as will be described in detail later. The first, second and third detector means 16 through 20 are respectively connected to input terminals of a control means 24 so as to apply the detected information to the control means 24 in the form of electric signals. The control means 24 may be, for example, a mini-computor. A temperature control means 26 and a humidity control means 28 are associated with the culture box 12 and connected to the output terminals of the control means 24 so as to control the temperature and humidity within the culture box 12 in accordance with the command or control signals from the control means 24, which control signals are based on the detected signals from the first detector means 16.

Gas containers 30, 32 and 34 which respectively contain $CO_2$ gas, $O_2$ gas and $N_2$ gas are connected to the culture box 12 through conduits 36, 38 and 40 which respectively communicate into the culture box 12. In order to control the supply of each gas into the culture box 12 control valves 42, 44 and 46 are disposed in the respective conduits 36, 38 and 40. Each of the control valves 42, 44 and 46 is connected to one of the output terminals of the control means 24 so as to be controlled by the control signal from the control means 24, which control signal is based on the detected signal from the first detector means 16 and 18. Specifically, the pH value of the nutrient solution in the container 14 is controlled by operating the control valve 42 by means of the control signal from the control means 24, which control signal is based on the detected signal from the second detector means 18.

A nutrient solution trough 48 containing a nutrient solution, a buffer solution trough 50 containing a buffer solution and an enzyme solution trough 54 containing an enzyme solution are respectively connected to the distributing means 22 through conduits 56, 58 and 60. Control valves 62, 64 and 66 similar to the valves 42, 44 and 46 are disposed in the conduits 56, 58 and 60, respectively, so as to control the supply of each solution into the distributing means 22. Each of the control valves 62, 64 and 66 is connected to different output terminals of the control means 24 and controlled by the control signal from the control means 24, which control signal is based on the detected signal from the third detector means 20.

In the present invention, the cells or tissues of the living body are cultivated in each of the containers 14 which are disposed in the gas-sealed culture box 12, so that the cells or tissues gradually multiply in the container 14. During the cultivation, the gaseous atmosphere, temperature and humidity in the culture box 12 and the pH value of the nutrient solution in the container 14 are continuously detected by the first and second detector means 16 and 18. Similarly, the multiplication conditions of the cells or tissues in each of the containers 14 are successively detected by the third detector means 20 as in the manner described before.

The control means 24 continuously compares detected signals from each detector means with the reference signals in the control means 24 and, in accordance with the results of such comparisons, generates the control signals to be applied to the temperature control means 26, humidity control means 28 and control valves 42 through 46 so that the gaseous atmosphere, temperature and humidity within the culture box 12 and the pH value of the nutrient solution in the containers 14 will be maintained in the desired optimum conditions. The control means 24 evaluates the multiplication conditions of the tissues or cells in the container 14 by processing the detected information from the third detector means 20 in the comparison and operational manner. For this purpose, it may be possible to use the information obtained by photoelectrically sorting the density of the tissues or cells or the intelligence obtained by sorting the image intelligence of the tissues or cells which is processed to denote the pattern of the density of the tissues or cells. When the control means 24 determines that the tissues or cells in one container 14 have multiplied in a sufficient quantity to be divided, the container 14 is moved to the position near the distributing means 22 by the moving mechanism, mentioned above and then the control signal is applied from the control means 24 to the distributing means so that the latter sucks up and discharges the nutrient solution out of the container 14. Subsequent to the discharge of the nutrient solution, the control means generates another control signal to be applied to the control valve 64 so that the buffer solution in the trough 50 is supplied to the container 14 through the distributing means 22. The buffer solution is used to clean the container 14 for predetermined periods of time and is discharged after such cleaning by the distributing means 22. Then the control valve 66 is opened by the control signal from the control means 24 and, as a result, the enzyme solution is supplied to the container 14 through the distributing means 22 in order to make the tissues or cells, which have adhered to the inner surfaces of the container 14 during their cultivation, come off from the container 14.

After these operations, the tissues or cells which came off the inside surfaces of the container 14 are put into a centrifugal separator which is installed in the culture box 12. The tissues or cells separated from the enzyme solution by the centrifugal separator are then diluted, divided into amounts of a predetermined quantity and put into the empty containers similar to the ones shown in FIG. 1 at 14 for further culturing or multiplication. These operations i.e. putting the tissues or cells into the container, dividing them in portions of a predetermined quantity and putting them into the empty container are mechanically and automatically performed by an operating mechanism (not shown) installed in the culture box 12. Since this operating mechanism per se as well as the moving mechanism for moving the container 14 does not constitute the essential part of the subject matter of the present invention, and since both of the mechanisms can be easily designed and used in conformity with the required operations, these mechanisms are ommitted from FIG. 1 and the detailed descriptions on these mechanisms are also ommitted in this specification.

FIG. 2 diagramatically shows the process of the tissue or cell culture according to the present invention, which has been described in detail above. In FIG. 2, reference numeral 80 represents injection of the divided tissues or cells into a culture container, reference numeral 82 represents culture of the tissues or cells, reference numeral 84 represents detection of the various culture conditions and of the multiplication condition of the tissues or cells, reference numeral 86 represents suction and discharge of the nutrient solution out of the culture container, reference numeral 88 represents injection of the buffer solution into the culture container, reference numeral 90 represents suction and discharge of the buffer solution out of the culture container, reference numeral 92 represents injection of the enzyme solution into the culture container, reference numeral 94 represents suction and discharge of the enzyme solution out of the culture container, and reference numeral 96 represents a process of the injection of the nutrient solution into an empty culture container.

What we claim is:

1. A method for automatically and successively cultivating tissues or cells of a living body which are contained, together with a nutrient solution, in culture containers with lids such as Petri dishes disposed in a gas-sealed culture box, said method comprising, in combination, the steps of:
   (1) injecting divided tissues or cells into said culture container together with the nutrient solution;
   (2) culturing the tissues or cells;
   (3) detecting culture conditions and multiplication condition of the tissues or cells;
   (4) sucking and discharging the nutrient solution out of said culture containers;
   (5) injecting a buffer solution into said culture container and cleaning the tissues or cells with the buffer solution;
   (6) sucking and discharging the buffer solution out of said culture containers;
   (7) injecting an enzyme solution into said culture containers thereby releasing the tissues or cells from the inner surfaces of said culture container;
   (8) separating the thus released tissues or cells from the enzyme solution by a centrifugal separator;
   (9) discharging the enzyme solution;
   (10) diluting the separated tissues or cells with fresh nutrient solution; and
   (11) injecting the diluted tissues or cells into empty culture containers with lids such as Petri dishes for further culture or multiplication;

and during said steps:
   (a) monitoring within said culture box, culture conditions, which conditions are represented by
      (i) temperature,
      (ii) humidity, and
      (iii) gaseous atmosphere of $CO_2$, $O_2$ and $N_2$ in said culture box, and
      (iv) the pH value of the nutrient solution:
   (b) detecting, within said culture box, a multiplication condition of the tissues or cells including detecting the pattern of the tissues or cells by detecting the density of the tissues or cells by a microscope, or by detecting the image information processed characterizing the pattern of the density of the tissues or cells by a microscope; and thereafter
   (c) controlling, within said culture box, said culture condition and apparatus for subculturing the tissues or cells in accordance with the information monitored and detected in said monitoring step (a) and said detecting step (b).

* * * * *